United States Patent [19]

Misawa et al.

[11] Patent Number: 5,302,705
[45] Date of Patent: Apr. 12, 1994

[54] 6-O-METHYLERYTHROMYCIN A OXIME DERIVATIVES

[75] Inventors: Yoko Misawa, Omiya; Toshifumi Asaka, Ageo; Masato Kashimura, Omiya; Shigeo Morimoto, Saitama; Yoshiaki Watanabe, Kodaira; Katsuo Hatayama, Omiya, all of Japan

[73] Assignee: Taisho Pharmaceutical Co., Ltd., Japan

[21] Appl. No.: 590,805

[22] Filed: Oct. 1, 1990

[30] Foreign Application Priority Data

Oct. 7, 1989 [JP] Japan ................. 1-262797

[51] Int. Cl.$^5$ ........................... C07H 17/08
[52] U.S. Cl. ................................. 536/7.4
[58] Field of Search ............... 536/7.4, 7.2; 514/29

[56] References Cited

U.S. PATENT DOCUMENTS

| | | | |
|---|---|---|---|
| 4,331,803 | 5/1982 | Watanabe et al. | 536/7.2 |
| 4,349,545 | 9/1982 | d'Ambrieres et al. | 514/29 |
| 4,680,386 | 7/1987 | Morimoto et al. | 536/7.4 |
| 4,740,502 | 4/1988 | Hannick et al. | 514/29 |
| 4,921,839 | 5/1990 | Brain et al. | 536/7.4 |

FOREIGN PATENT DOCUMENTS

| | | | |
|---|---|---|---|
| 0158467 | 10/1985 | European Pat. Off. | 536/7.4 |
| 0195960 | 1/1986 | European Pat. Off. | |
| 0194833 | 3/1986 | European Pat. Off. | 536/7.4 |
| 0201166 | 12/1986 | European Pat. Off. | |
| 0245013 | 4/1987 | European Pat. Off. | 536/7.1 |
| 0260938 | 3/1988 | European Pat. Off. | |

Primary Examiner—Johnnie R. Brown
Assistant Examiner—Elli Pesele
Attorney, Agent, or Firm—Lorusso & Loud

[57] ABSTRACT

A 6-0-methylerythromycin A oxime derivative represented by the formula

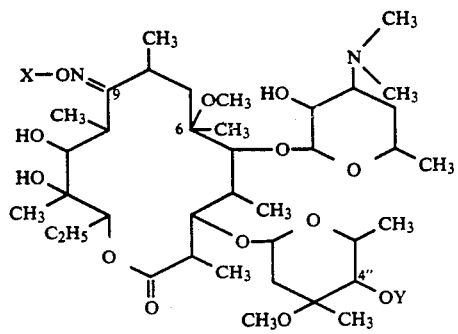

wherein X is a substituted benzyl group, a substituted phenyl group, an $\alpha$-methylbenzyl group, an $\alpha$-methylphenethyl group, a diphenylmethyl group, a trityl group, a dibenzosuberanyl group, or a group of the formula $-(CH_2)_n-R$, and Y is a hydrogen atom, a substituted phenyl group or a 2-aminothiazol-4-ylmethylcarbonyl group, and a pharmaceutically acceptable salt thereof are disclosed. These compounds have antibacterial activity against erythromycin resistant bacteria.

1 Claim, No Drawings

6-O-METHYLERYTHROMYCIN A OXIME DERIVATIVES

BACKGROUND OF THE INVENTION (1) Field of the Invention

The present invention relates to novel antibiotic erythromycin derivatives, and more particularly relates to novel 6-0-methylerythromycin A 9-oxime derivatives and the salts thereof having strong antibacterial activity against erythromycin resistant bacteria.

(2) Prior Art

Erythromycin A is an antibiotic which is widely clinically used as a therapeutical agent for treatment of infectious diseases caused by many Gram-positive bacteria, a certain Gram-negative bacteria and mycoplasma. The main disadvantage of erythromycin A is low acid-stability which leads to low and inconsistent oral absorption. Among Gram-positive bacteria are known bacteria which have lower sensitivity to erythromycin A than to the other pathogenic bacteria and are resistant to erythromycin A. In order to improve such biological and pharmacodynamical properties of erythromycin A, many derivatives have been prepared. For example, there are disclosed erythromycin 9-oxime ether derivatives in U.S. Pat. No. 4,349,545, 6-0-methylerythromycin derivatives in U.S. Pat. Nos. 4,331,803 and 4,680,386 and E.P. Patent No. 245,013.

The above-mentioned derivatives solved moderately the problem of the low acid-stability which is a disadvantage of erythromycin. Accordingly, these derivatives are known to show more excellent in vivo antibacterial activity than erythromycin when administered orally. However, the problem of resistant bacteria against erythromycin A has not yet been sufficiently solved.

E.P. Patent No. 194,833 discloses a series of 6-0-methylerythromycin 9-oxime ether derivatives. However, this patent discloses only a methyl ether derivative in the working example and does not report any activity against erythromycin resistant bacteria.

The present inventors have found that some 6-0-methylerythromycin A 9-oxime derivatives have strong antibacterial activity against erythromycin resistant bacteria.

SUMMARY OF THE INVENTION

An object of the present invention is to provide a 6-0-methylerythromycin A 9-oxime derivative represented by the formula

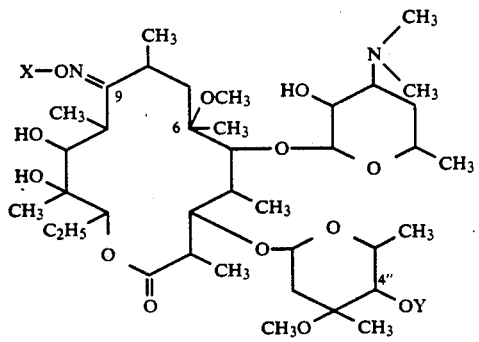

wherein X is a benzyl group substituted on the benzene ring by 1 to 5 members selected from the group consisting of a halogen atom, an alkyl group having 1 to 5 carbon atoms, a nitro group, a trifluoromethyl group, a phenyl group, a benzyl group, a styryl group, a 2-chlorobenzyloxy group, a 3-(4-chlorophenyl)-1,2,4-oxadiazol-5-yl group and a 2-methoxycarbonylbenzoyl group; a phenyl group substituted by 1 to 3 nitro groups; an α-methylbenzyl group; an α-methylphenethyl group; a diphenylmethyl group; a trityl group; a dibenzosuberanyl group; or a group of the formula —$(CH_2)_n$—R (wherein R is a benzyl group, a phenylthio group, a phenylthio group substituted by a halogen atom, a cycloalkyl group having 5 or 6 carbon atoms, a naphthyl group, an anthracenyl group, a quinolyl group, a styryl group, a norbornyl group, a 5-chloro-2-thienyl group, a 2-benzyloxycarbonylaminothiazol-4-yl group, a phthalimide group, a 9-bromo-9-fluorenyl group, a 1-alkoxycarbonylmethylindol-3-yl group of which alkoxy group has 1 to 3 carbon atoms, a 4-(pyrid-2-yl)piperazyl group or a pyridyl group substituted by 1 or 2 members selected from the group consisting of a halogen atom and a 2,2,2-trifluoroethoxy group, and n is an integer of from 1 to 6), Y is a hydrogen atom, a phenyl group substituted by a nitro group, or a 2-aminothiazol-4-yl-methylcarbonyl group, and a pharmaceutically acceptable salt thereof.

DETAILED DESCRIPTION OF THE INVENTION

In the present invention, the alkyl group having 1 to 5 carbon atoms refers to a straight or branched chain alkyl group such as, for example, a methyl group, an ethyl group, a propyl group, an isopropyl group, a butyl group and a t-butyl group. The alkoxy group having 1 to 3 carbon atoms as part of the 1-alkoxycarbonylmethylindol-3-yl group refers to, for example, a methoxy group, an ethoxy group and an isopropoxy group. The halogen atom refers to a fluorine atom, a chlorine atom, a bromine atom and an iodine atom.

The pharmaceutically acceptable salts of the present invention include salts with acids such as hydrochloric acid, hydrobromic acid, sulfuric acid, phosphoric acid, formic acid, acetic acid, propionic acid, butyric acid, citric acid, glycolic acid, lactic acid, tartaric acid, malic acid, maleic acid, fumaric acid, gluconic acid, oxalic acid, stearic acid, manderic acid, thiocyanic acid, benzoic acid, succinic acid, p-toluenesulfonic acid, benzenesulfonic acid, methane-sulfonic acid, laurylsulfonic acid, aspartic acid, glutamic acid, adipic acid, cysteine, nicotinic acid, acrylic acid polymer and carboxyvinyl polymer.

The compounds of Formula I of the present invention exist in two isomers (E- and Z-forms) derived from the 9-oxime group. The present invention is not limited to one of the two isomers, but E-form is preferred.

Among the preferred compounds of the present invention are those of Formula I wherein X is benzyl group substituted on the benzene ring by an alkyl group having 1 to 5 carbon atoms or a halogen atom, or a group of the formula —$(CH_2)_n$—R (wherein R is an anthracenyl group and n is an integer of from 1 to 3). Most preferred compounds are those wherein X is an anthracenylmethyl group, a 2,4,6-trimethylbenzyl group and a 4-(t-butyl)benzyl group.

The compounds of the present invention can be, for example, prepared as follows:

6-0-Methylerythromycin A 9-oxime (known in U.S. Pat. No. 4,680,386), after being dissolved in a suitable organic solvent, is reacted with a compound of the formula X-Z (wherein X is as defined above, and Z is a halogen atom), in the presence of a base, to give a compound of Formula I in good yields. Suitable organic solvent used here means, for example, acetone, tetrahydrofuran, N,N-dimethylformamide, dimethyl sulfoxide and a mixture thereof. Base refers to, for example, sodium hydride, sodium hydroxide and potassium hydroxide. The reaction temperature is from −20° to 50° C., and preferably from 0° to 25° C.

The compounds of the present invention have strong antibacterial activity against Gram-positive and Gram-negative bacteria including erythromycin A resistant bacteria, and therefore, they are useful as antibacterial agents for the treatment of bacterial infectious diseases in human and animals including farm animals.

The compounds of the present invention can be administered orally or parenterally in a dosage form such as tablets, capsules, powders, troches, ointments, suspensions, suppositories and injectional solutions, all of which can be prepared according to the conventional pharmaceutical practices.

The daily dosage of the compound of Formula I in an adult human may be from about 50 to 3000 mg per day in single or up to three divided doses.

The compounds of Formula I have low toxicity. The $LD_{50}$ value in the case of oral administration is more than 2000 mg/kg in mice.

EXPERIMENT [IN VITRO ANTIBACTERIAL ACTIVITY]

The in vitro antibacterial activity of the compounds of the present invention against various test bacteria was measured by an agar dilution technique using sensitivity test agar (Eiken) as a test medium according to the MIC method specified by the Japan Chemotherapeutic Society.

As comparative drugs, there were used erythromycin A, 6-O-methylerythromycin A, erythromycin A 9-methoxyethoxymethyloxime (roxithromycin) and 6-O-methylerythromycin A 9-methyloxime.

The results are represented by the MIC value (minimum inhibitory concentration to microorganisms, mcg/ml), and shown in Table 1.

Symbols for the test drugs of Table 1 mean the following compounds.

a; Erythromycin A
b; 6-O-Methylerythromycin A
c; Roxithromycin
d; 6-O-Methylerythromycin A 9-methyloxime
A; Compound No. 7 in Example described below.
B; Compound No. 2 in Example described below.
C; Compound No. 35 in Example described below.
D; Compound No. 4 in Example described below.
E; Compound No. 8 in Example described below.
F; Compound No. 1 in Example described below.
G; Compound No. 56 in Example described below.
H; Compound No. 55 in Example described below.
I; Compound No. 45 in Example described below.

TABLE 1

| | In vitro antibacterial activity MIC value (mcg/ml) | |
|---|---|---|
| | Bacteria | |
| Test drug | S. aureus J-109 | S. aureus B1 |
| a | >100 | >100 |
| b | >100 | >100 |
| c | >100 | >100 |
| d | >100 | >100 |
| A | 6.25 | 6.25 |

TABLE 1-continued

| | In vitro antibacterial activity MIC value (mcg/ml) | |
|---|---|---|
| | Bacteria | |
| Test drug | S. aureus J-109 | S. aureus B1 |
| B | 6.25 | 6.25 |
| C | 25 | 50 |
| D | 12.5 | 12.5 |
| E | 12.5 | 12.5 |
| F | 6.25 | 6.25 |
| G | 25 | 25 |
| H | 12.5 | 12.5 |
| I | 12.5 | 12.5 |

The present invention is illustrated in more detail by the following examples. Examples 1 to 7 indicate the compounds of the present invention obtained by using the typical preparation methods a to g, and Table 2 lists the compounds of the present invention with their physical properties and preparation methods.

EXAMPLE 1 (PREPARATION METHOD a)

Preparation of 6-O-methylerythromycin A 9-[O-(2,4,6-trimethylbenzyl)oxime]

To a solution of 6-O-methylerythromycin A 9-oxime (1 g, 1.31 mmole) in tetrahydrofuran (20 ml) were added tetrabutylammonium iodide (25 mg, 0.07 mmole), 2,4,6-trimethylbenzyl chloride (331 mg, 1.96 mmol) and 85% potassium hydroxide powder (103 mg, 1.56 mmole), and the mixture was stirred at room temperature for 20 hours. The reaction mixture was extracted with ethyl acetate, and the ethyl acetate layer was washed with a saturated aqueous sodium chloride solution and dried over anhydrous magnesium sulfate. The ethyl acetate was evaporated under reduced pressure, and the residue was purified by silica gel column chromatography (eluent; chloroform: methanol: ammonia=19:1:0.1) to give 813 mg of the title compound (Compound No. 1) as a white crystalline powder.

EXAMPLE 2 (PREPARATION METHOD b)

Preparation of 6-O-methylerythromycin A 9-[O-(α-methylbenzyl)oxime]

A mixture of 6-O-methylerythromycin A 9-oxime (1 g, 1.31 mmole), α-methylbenzyl bromide (0.54 ml, 3.93 mmole), 85% potassium hydroxide powder (103 mg, 1.56 mmole) and N,N-dimethylformamide (20 ml) was stirred with ice-cooling for 2.5 hours. Then, following work up similar to that of Example 1, there was obtained 730 mg of the title compound (Compound No. 4) as a white foam.

EXAMPLE 3 (PREPARATION METHOD c)

Preparation of 6-O-methylerythromycin A 9-[O-(diphenylmethyl)oxime]

To a solution of 6-O-methylerythromycin A 9-oxime (2 g, 2.62 mmole) in N,N-dimethylformamide (40 ml) were added diphenylmethyl chloride (1.4 ml, 7.87 mmole) and 60% sodium hydride (158 mg, 3.95 mmole) with ice-cooling, and the mixture was stirred at room temperature for 7 hours. Then, following extraction and purification similar to those of Example 1, there was obtained 720 mg of the title compound (Compound No. 9) as a white foam.

EXAMPLE 4 (PREPARATION METHOD d)

Preparations of 6-0-methylerythromycin A 9-[0-(2-nitrophenyl)oxime] (a) and 4"-0-(2-nitrophenyl)-6-0-methylerythromycin A 9-[[0-(2-nitrophenyl)oxime] (b)

To a solution of 6-0-methylerythromycin A 9-oxime (5.33 g, 7 mmole) in dioxane (80 ml) were added 2-fluoronitrobenzene (1.1 ml, 10.5 mmole) and 60% sodium hydride (336 mg, 8.4 mmole) with ice-cooling, and the mixture was stirred at room temperature for 2 hours. Then, following extraction, isolation and purification steps similar to those of Example 1, there were obtained 3.92 g of the title compound (a) [Compound No. 27(a)] and 730 mg of the title compound (b) [Compound No. 27(b)], each of which was a yellow foam.

EXAMPLE 5 (PREPARATION METHOD e)

Preparation of 6-0-methylerythromycin A 9-[0-(trityl)oxime]

To a solution of 6-0-methylerythromycin A 9-oxime (2 g, 2.62 mmole) in N,N-dimethylformamide (20 ml) were added trityl chloride (1.1 g, 5.24 mmole) and triethylamine (2 ml, 14.35 mmole), and the mixture was stirred at room temperature for 6 hours. Then, following extraction and purification steps similar to those of Example 1, there was obtained 60 mg of the title compound (Compound No. 40) as a white foam.

EXAMPLE 6 (PREPARATION METHOD f)

Preparation of 6-0-methylerythromycin A 9-[0-(2-benzyloxycarbonylaminothiazol-4-ylmethyl)oxime]

To a solution of 6-0-methylerythromycin A 9-oxime (3 g, 3.93 mmole) in tetrahydrofuran (50 ml) were added 2-benzyloxycarbonylamino-4-chloromethylthiazole (1.2 mg, 4.2 mmole), tetrabutylammonium iodide (144 mg, 0.39 mmole) and 60% sodium hydride (472 mg, 11.8 mmole). Following a procedure similar to that of Example 1, there was obtained 1.12 g of the title compound (Compound No. 41) as a pale yellow foam.

EXAMPLE 7 (PREPARATION METHOD g)

Preparation of 4"-0-(2-aminothiazol-4-yl)methylcarbonyl-6-0-methylerythromycin A 9-[0-(2,4,6-trimethylbenzyl)oxime]

To a solution of the compound (447 mg, 0.5 mmole) obtained in Example 1 in dichloromethane (5 ml) were added at −70° C. sodium bicarbonate (84 mg, 1 mmole) and bromoacetoacetyl bromide (122 mg, 0.5 mmole), and the mixture was stirred at −70° C. for 5 minutes then at room temperature for 30 minutes. After evaporation of the dichloromethane under reduced pressure, the residue was dissolved in N,N-dimethylacetamide (5 ml), thiourea (76 mg, 1.0 mmole) was added thereto, and the mixture was stirred at room temperature for 17 hours. The reaction solution was extracted with ethyl acetate and washed with a saturated aqueous sodium chloride solution, and the ethyl acetate layer was dried over anhydrous magnesium sulfate. The ethyl acetate was evaporated under reduced pressure, and the residue was purified by silica gel column chromatography (eluent; chloroform: methanol: ammonia=95:5:0.1) to give 170 mg of the title compound (Compound No. 44) as an orange yellow foam.

TABLE 2

| Compound No. | X | Y | ¹H-NMR(CDCl₃) δ (ppm) | Physical properties except for ¹H NMR | Preparation method |
|---|---|---|---|---|---|
| 1 | 3,5-dimethylbenzyl (–CH₂–C₆H₃(CH₃)₂) | H | 2.22(3H, s)<br>2.28(6H, s)<br>2.35(6H, s)<br>2.35(6H, s)<br>3.03(3H, s)<br>3.31(3H, s)<br>4.60(1H, s)<br>5.05(2H, s)<br>6.84(2H, s) | m.p. 198~202° C.<br>(recrystallized from ethyl acetate)<br>Mass(FAB)<br>m/z; 895[MH]⁺ | a |
| 2 | 4-tert-butylbenzyl (–CH₂–C₆H₄–C₄H₉-t) | H | 1.32(9H, s)<br>2.28(6H, s)<br>3.05(3H, s)<br>3.33(3H, s)<br>4.63(1H, s)<br>4.99, 5.00(2H, ABq)<br>7.26, 7.30, 7.36, 7.40(4H) | m.p. 138~141° C.<br>(recrystallized from methanol)<br>Mass(FAB)<br>m/z; 909[MH]⁺ | a |
| 3 | pentafluorobenzyl (–CH₂–C₆F₅) | H | 2.28(6H, s)<br>3.02(3H, s)<br>3.33(3H, s)<br>4.25(1H, s)<br>5.08, 5.09(2H, ABq) | m.p. 177~178° C.<br>(recrystallized from methanol)<br>Mass(FAB)<br>m/z; 943[MH]⁺ | a |
| 4 | 1-phenylethyl (CH₃–CH–C₆H₅) | H | 2.40(6H, s)<br>3.15(3H, s)<br>3.32(3H, s)<br>3.34(3H, s)<br>7.23~7.35(5H, m) | | b |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 5 | —(CH$_2$)$_3$—phenyl | H | 2.29(6H, s)<br>3.06(3H, s)<br>3.33(3H, s)<br>4.64(1H, s)<br>7.15~7.36(5H, m) | | b |
| 6 | —CH$_2$S—(4-Cl-phenyl) | H | 2.30(6H, s)<br>2.94(3H, s)<br>3.31(3H, s)<br>4.20(1H, s)<br>5.36, 5.44(2H, ABq, J=11Hz)<br>7.22, 7.26, 7.34, 7.38(4H) | Mass(FAB)<br>m/z; 919[MH]$^+$ | a |
| 7 | —CH$_2$—(9-anthracenyl) | H | 2.25(6H, s)<br>2.88(3H, s)<br>3.30(3H, s)<br>4.48(1H, s)<br>6.00(2H, ABq)<br>7.41~7.57, 7.97~8.03,<br>8.38~8.45(9H, m) | Mass(FAB)<br>m/z; 953[MH]$^+$ | b |
| 8 | —CH$_2$—(2,6-difluorophenyl) | H | 2.31(6H, s)<br>2.89(3H, s)<br>3.31(3H, s)<br>4.43(1H, s)<br>5.09(2H, ABq)<br>6.75~6.97, 7.19~7.34<br>(3H, m) | | a |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 9 | -CH(C$_6$H$_5$)$_2$ (diphenylmethyl) | H | 2.46(6H, s)<br>2.95(3H, s)<br>3.31(3H, s)<br>4.35(1H, s)<br>6.60(1H, s)<br>7.19~7.41(10H, m) | Mass(FAB)<br>m/z; 929[MH]$^+$ | c |
| 10 | -CH$_2$-(3-chlorophenyl) | H | 2.29(6H, s)<br>3.06(3H, s)<br>3.33(3H, s)<br>4.46(1H, s)<br>4.99, 5.00(2H, ABq)<br>7.17~7.32(4H, m) | | b |
| 11 | -CH$_2$-(2,4-dimethylphenyl) | H | 2.24(6H, s)<br>3.05(3H, s)<br>3.33(3H, s)<br>7.05~7.20(3H, m) | | a |
| 12 | -CH$_2$-(1-naphthyl) | H | 2.27(6H, s)<br>2.91(3H, s)<br>3.31(3H, s)<br>4.58(1H, s)<br>5.44, 5.54(2H, ABq, J=11Hz)<br>7.40~7.55, 7.78~7.89,<br>8.07~8.14(7H, m) | | a |

TABLE 2-continued

[Core macrolide structure with X—O—N= and —O—Y substituents]

| Compound No. | X | Y | $^1$H-NMR(CDCl$_3$) δ (ppm) | Physical properties except for $^1$H NMR | Preparation method |
|---|---|---|---|---|---|
| 13 | 2,4-dimethylbenzyl (—CH$_2$-C$_6$H$_3$(CH$_3$)$_2$) | H | 2.30(6H, s)<br>2.32(6H, s)<br>3.04(3H, s)<br>3.31(3H, s)<br>6.95~7.20(3H, m) | | a |
| 14 | 2,4-dimethylbenzyl | H | 2.30(6H, s)<br>2.31(6H, s)<br>3.03(3H, s)<br>3.31(3H, s)<br>5.00, 5.02(2H, ABq, J=11Hz)<br>6.98~7.20(3H, m) | | a |
| 15 | 4-phenylbenzyl (biphenylmethyl) | H | 2.28(6H, s)<br>3.09(3H, s)<br>3.33(3H, s)<br>4.62(1H, s)<br>5.06, 5.07(2H, ABq, J=12Hz)<br>7.30~7.49, 7.57~7.64 (8H, m) | | a |
| 16 | pentamethylbenzyl | H | 2.23(6H, s)<br>2.25(3H, s)<br>2.30(6H, s)<br>2.32(6H, s)<br>3.07(3H, s)<br>3.32(3H, s)<br>4.69(1H, s)<br>5.11, 5.13(2H, ABq, J=12Hz) | Mass(FAB)<br>m/z; 923[MH]$^+$ | a |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 17 | 5-chloro-2-thienyl-CH$_2$— | H | 2.62(6H, s)<br>3.03(3H, s)<br>3.31(3H, s)<br>5.02, 5.03(2H, ABq, J=11Hz)<br>6.78(2H, s) | | a |
| 18 | —CH$_2$—CH=CH—phenyl | H | 2.33(6H, s)<br>3.11(3H, s)<br>3.33(3H, s)<br>6.26~6.41(1H)<br>6.59, 6.66(1H)<br>7.20~7.42(5H, m) | | a |
| 19 | phenyl-CH$_2$S— | H | 2.43(6H, s)<br>2.93(3H, s)<br>3.31(3H, s)<br>4.27(1H, s)<br>5.41, 5.46(2H, ABq, J=12Hz)<br>7.15~7.48(5H, m) | | a |
| 20 | 2-methylphenyl-CH$_2$— | H | 2.29(6H, s)<br>2.34(3H, s)<br>3.02(3H, s)<br>3.32(3H, s)<br>4.57(1H, s)<br>5.03, 5.06(2H, ABq, J=11Hz)<br>7.13~7.35(4H, m) | | b |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 21 | 3-CH$_3$-C$_6$H$_4$-CH$_2$- | H | 2.35(6H, s)<br>2.37(3H, s)<br>3.04(3H, s)<br>3.32(3H, s)<br>4.58(1H, s)<br>4.98, 5.00(2H, ABq, J=12Hz)<br>7.09~7.29(4H, m) | | a |
| 22 | 4-CH$_3$-C$_6$H$_4$-CH$_2$- | H | 2.28(6H, s)<br>2.35(3H, s)<br>3.05(3H, s)<br>3.32(3H, s)<br>4.61(1H, s)<br>4.97, 4.99(2H, ABq, J=11Hz)<br>7.14, 7.18, 7.23, 7.27(4H, m) | | a |
| 23 | 2-CF$_3$-C$_6$H$_4$-CH$_2$- | H | 2.29(6H, s)<br>3.04(3H, s)<br>3.33(3H, s)<br>4.41(1H, s)<br>5.24(2H, ABq)<br>7.34~7.68(4H, m) | | a |
| 24 | 4-F-C$_6$H$_4$-CH$_2$- | H | 2.29(6H, s)<br>3.03(3H, s)<br>3.32(3H, s)<br>4.53(1H, s)<br>4.95, 4.97(2H, ABq, J=10Hz)<br>6.99~7.06, 7.28~7.37(4H) | | a |

TABLE 2-continued

[Structure of macrolide compound with X—O—N= group and O—Y group]

| Compound No. | X | Y | ¹H-NMR(CDCl₃) δ (ppm) | Physical properties except for ¹H NMR | Preparation method |
|---|---|---|---|---|---|
| 25 | 3-F-C₆H₄-CH₂- | H | 2.30(6H, s) 3.06(3H, s) 3.34(3H, s) 4.48(1H, s) 5.00, 5.02(2H, ABq) 6.92~7.12, 7.25~7.36 (4H, m) | | a |
| 26 | 2-F-C₆H₄-CH₂- | H | 2.29(6H, s) 2.99(3H, s) 3.34(3H, s) 4.45(1H, s) 5.09(2H, ABq) 7.00~7.18, 7.21~7.44 (4H, m) | | a |
| 27 (a) | 2-O₂N-C₆H₄- | H | 2.29(6H, s) 3.00(3H, s) 3.33(3H, s) 7.01~7.11, 7.49~7.59, 7.93, 7.99(4H, m) | | d |
| 27 (b) | 2-O₂N-C₆H₄- | 2-O₂N-C₆H₄- | 2.33(6H, s) 2.99(3H, s) 3.35(3H, s) 6.97~7.15(3H, m) 7.43~7.97(5H, m) | | d |

TABLE 2-continued
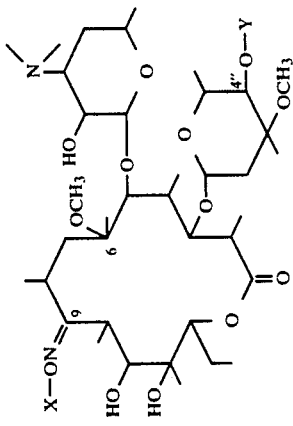
| Compound No. | X | Y | $^1$H-NMR(CDCl$_3$) δ (ppm) | Physical properties except for $^1$H NMR | Preparation method |
|---|---|---|---|---|---|
| 28 | 2,4-dinitrophenyl | H | 2.30(6H, s)<br>2.99(3H, s)<br>3.33(3H, s)<br>7.77, 7.82(1H)<br>8.40, 8.41, 8.43, 8.44(1H)<br>8.90, 8.91(1H) | | d |
| 29 | —CH$_2$—(3-nitrophenyl) | H | 2.27(6H, s)<br>3.07(3H, s)<br>3.32(3H, s)<br>4.36(1H, s)<br>5.11, 5.13(2H, ABq, J=13Hz)<br>7.50~7.67(2H, m)<br>8.13~8.25(2H, m) | | a |
| 30 | —CH$_2$-(quinolin-2-yl) | H | 2.29(6H, s)<br>3.11(3H, s)<br>3.33(3H, s)<br>4.41(1H, s)<br>5.31, 5.32(2H, ABq)<br>7.49~7.56(2H, m)<br>7.66~7.73(2H, m)<br>8.05~8.19(2H, m) | | b |
| 31 | —CH$_2$CH$_2$—phenyl | H | 2.29(6H, s)<br>2.95(3H, s)<br>3.33(3H, s)<br>4.63(1H, s)<br>7.14~7.33(5H, m) | | a |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 32 | phthalimido-CH$_2$- | H | 2.38(6H, s)<br>2.91(3H, s)<br>3.31(3H, s)<br>4.39(1H, s)<br>5.56(2H, s)<br>7.71~7.95(4H, m) | | c |
| 33 | 2,6-dichlorobenzyl (-CH$_2$-C$_6$H$_3$Cl$_2$) | H | 2.29(6H, s)<br>2.94(3H, s)<br>3.31(3H, s)<br>4.39(1H, s)<br>5.31, 5.32(2H, ABq, J=11Hz)<br>7.11~7.34(3H, m) | | a |
| 34 | 4-(2-phenylethenyl)benzyl | H | 2.28(6H, s)<br>3.07(3H, s)<br>3.33(3H, s)<br>4.60(1H, s)<br>5.01, 5.03(2H, ABq, J=12Hz)<br>7.11(2H)7.20~7.41(5H, m)<br>7.50~7.54(4H, m) | | b |
| 35 | cyclohexyl-CH$_2$- | H | 2.38(6H, s)<br>3.06(3H, s)<br>3.32(3H, s) | | a |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 36 | (10,11-dihydro-5H-dibenzo[a,d]cyclohepten-5-yl) | H | 2.41, 2.46(6H, 2H) 3.04(3H, s) 3.33(3H, s) 6.00(1H, s) 7.09~7.56(8H, m) | | b |
| 37 | (9-bromo-9H-fluoren-9-yl)CH$_2$— | H | 2.41, 2.46(6H) 3.05, 3.06(3H) 3.33, 3.34(3H) 7.25~7.81(8H) | | b |
| 38 | 3-[(4-chlorophenyl)-1,2,4-oxadiazol-5-yl]phenyl-CH$_2$— | H | 2.29(6H, s) 3.10(3H, s) 3.34(3H, s) 7.47~7.61(4H, m) 8.08~8.22(4H, m) | | a |
| 39 | 3-(2-(N-ethoxycarbonylmethyl-indol-3-yl))ethyl—CH$_2$CH$_2$— | H | 2.38(6H, s) 2.98(3H, s) 3.33(3H, s) 4.21(2H, q, J=7Hz) 7.23~7.29(4H, m) 7.56~7.62(1H, m) | | b |
| 40 | trityl group | H | 2.30(6H, s) 3.31(3H, s) 7.16~7.40(15H, m) | Mass(FAB) m/z; 1005[MH]$^+$ | c |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 41 | ![structure with CH$_2$=C(CH$_3$)-S-C(=N-)-NHCO$_2$CH$_2$-phenyl] | H | 2.28(6H, s)<br>2.62(3H, s)<br>3.32(3H, s)<br>5.77(1H, s)<br>6.73(1H, s)<br>7.25~7.43(5H, m) | | f |
| 42 | ![2-chlorobenzyl: -CH$_2$-C$_6$H$_4$-Cl] | H | 1.43(3H, s)<br>2.33(6H, s)<br>3.01(3H, s)<br>3.32(3H, s)<br>5.10, 5.17<br>(2H, ABq, J$_{AB}$=13.8Hz)<br>7.19~7.44(4H, m) | m.p. 145~147° C. (recrystallized from ethanol - petroleum ether) IR(KBr)cm$^{-1}$; 3431, 1734 $^{13}$C-NMR (75MHz, CDCl$_3$) δ(ppm): 175.6, 171.1, 153.8, 133.3, 129.6, 129.3, 128.8, 126.6, 78.7, 74.0, 72.7, 50.8, 49.5, 40.3 | a |
| 43 | ![CH$_3$-CH(CH$_2$-)-phenyl] | H | 2.33(6H, s)<br>3.09, 3.11(3H, s)<br>3.34(3H, s)<br>7.13~7.40(5H, m) | | a |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 44 | 2,4,6-trimethylbenzyl (—CH$_2$–C$_6$H$_2$(CH$_3$)$_3$) | —CO—CH$_2$—C(=N)(NH$_2$)S (thiazoline-type) | 2.25(3H, s)<br>2.36, 2.39(9H, s)<br>3.01(3H, s)<br>3.30(3H, s)<br>6.42(1H, s)<br>6.84(2H, s) | | g |
| 45 | norbornyl-CH$_2$— | H | 2.40(6H, s)<br>3.08(3H, s)<br>3.33(3H, s) | | a |
| 46 | 2,6-dichloropyridin-4-ylmethyl | H | 2.37(6H, s)<br>3.10(3H, s)<br>3.34(3H, s)<br>7.20(2H, s) | | a |
| 47 | 3,5-dibromobenzyl | H | 2.33(6H, s)<br>3.08(3H, s)<br>3.33(3H, s)<br>7.40~7.58(3H, m) | | b |

TABLE 2-continued

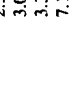

| Compound No. | X | Y | $^1$H-NMR(CDCl$_3$) δ (ppm) | Physical properties except for $^1$H NMR | Preparation method |
|---|---|---|---|---|---|
| 48 | —(CH$_2$)$_5$—C$_6$H$_5$ | H | 2.38(6H, s) 3.06(3H, s) 3.33(3H, s) 7.11~7.32(5H, m) | | a |
| 49 | —CH$_2$—(2-Cl, 6-F-C$_6$H$_3$) | H | 2.28(6H, s) 2.90(3H, s) 3.32(3H, s) 5.20(2H, m) 6.95~7.30(3H, m) | m.p. 163~165° C. (recrystallized from ethanol) Mass(FAB) m/z; 905[MH]$^+$ IR(KBr)cm$^{-1}$; 3470, 1734 | a |
| 50 | —CH$_2$—(2-CH$_3$, 6-F-C$_6$H$_3$) | H | 2.27(3H, d) 2.36(6H, s) 2.98(3H, s) 3.32(3H, s) 5.07(2H, m) 6.95~7.25(3H, m) | Mass(FAB) m/z; 885[MH]$^+$ IR(KBr)cm$^{-1}$; 3436, 1735 | a |
| 51 | —(CH$_2$)$_3$—N(piperazinyl)-2-pyridyl | H | 2.33(6H, s) 3.08(3H, s) 3.33(3H, s) 6.59~6.71(2H, m) 7.44~7.51(1H, m) 8.17~8.21(1H, m) | Mass(FAB) m/z; 966[MH]$^+$ IR(KBr)cm$^{-1}$; 3436, 1734 | a |

TABLE 2-continued

| Compound No. | X | Y | $^1$H-NMR(CDCl$_3$) δ (ppm) | Physical properties except for $^1$H NMR | Preparation method |
|---|---|---|---|---|---|
| 52 | 4-(2-CO₂CH₃-benzoyl)benzyl (—CH₂-C₆H₄-CO-C₆H₄-CO₂CH₃) | H | 2.43(6H, s)<br>3.05(3H, s)<br>3.31(3H, s)<br>3.61(3H, s)<br>5.04, 5.10(2H, ABq, J$_{AB}$=13Hz)<br>7.38~8.08(8H, m) | m.p. 137~139° C.<br>(recrystallized from methanol)<br>Mass(FAB)<br>m/z; 1015[MH]$^+$<br>IR(KBr)cm$^{-1}$;<br>3446, 1730, 1673<br>1609 | a |
| 53 | 2-benzylbenzyl (—CH₂-C₆H₄-CH₂Ph) | H | 2.29(6H, s)<br>3.01(3H, s)<br>3.32(3H, s)<br>4.08(2H, s)<br>4.96, 5.07(2H, ABq, J$_{AB}$=12Hz)<br>7.10~7.38(9H, m) | m.p. 168~170° C.<br>(recrystallized from methanol)<br>Mass(FAB)<br>m/z; 963[MH]$^+$<br>IR(KBr)cm$^{-1}$;<br>3457, 1736 | a |
| 54 | 2-(phenoxymethyl)benzyl (—CH₂-C₆H₄-CH₂-O-C₆H₅) | H | 2.30(6H, s)<br>3.04(3H, s)<br>3.33(3H, s)<br>4.92, 4.95(2H, ABq, J$_{AB}$=12Hz)<br>5.18(2H, s)<br>6.94~7.58(8H, m) | m.p. 111~113° C.<br>(recrystallized from hexane)<br>Mass(FAB)<br>m/z; 993[MH]$^+$<br>IR(KBr)cm$^{-1}$;<br>3436, 1734, 1613 | a |
| 55 | 4-isopropylbenzyl (—CH₂-C₆H₄-C₃H₇-i) | H | 2.29(6H, s)<br>3.04(3H, s)<br>3.33(3H, s)<br>4.96, 5.02(2H, ABq, J$_{AB}$=12Hz)<br>7.18~7.32(4H, m) | m.p. 149~151° C.<br>(recrystallized from methanol)<br>Mass(FAB)<br>m/z; 895[MH]$^+$<br>IR(KBr)cm$^{-1}$;<br>3458, 1736, 1632 | a |

TABLE 2-continued

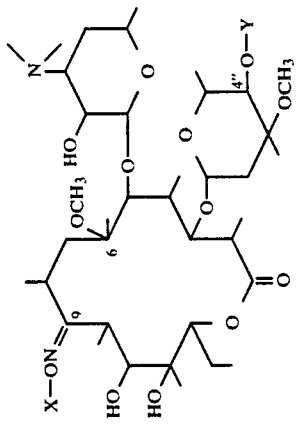

| Compound No. | X | Y | $^1$H-NMR(CDCl$_3$) δ (ppm) | Physical properties except for $^1$H NMR | Preparation method |
|---|---|---|---|---|---|
| 56 | —(CH$_2$)$_4$— phenyl | H | 2.32(6H, s) 3.06(3H, s) 3.33(2H, s) 7.13~7.30(5H, m) | m.p. 96~98° C. Mass(FAB) m/z; 895[MH]$^+$ IR(KBr)cm$^{-1}$; 3456, 1735 | a |
| 57 | —CH$_2$— (2-bromophenyl) | H | 2.29(6H, s) 3.02(3H, s) 3.33(3H, s) 5.07, 5.15(2H, ABq, J$_{AB}$=13Hz) 7.10~7.58(4H, m) | m.p. 139~141° C. (recrystallized from methanol) Mass(FAB) m/z; 931[MH]$^+$ IR(KBr)cm$^{-1}$; 3464, 1734 | a |
| 58 | —CH$_2$— (3,5-difluorophenyl) | H | 2.31(6H, s) 3.07(3H, s) 3.33(3H, s) 4.95, 5.02(2H, ABq, J$_{AB}$=13Hz) 6.68~6.76(1H, m) 6.80~6.88(2H, m) | m.p. 129~131° C. (recrystallized from methanol) Mass(FAB) m/z; 889[MH]$^+$ IR(KBr)cm$^{-1}$; 3473, 1733, 1628 | a |
| 59 | —CH$_2$— (4-chlorophenyl) | H | 2.29(6H, s) 3.05(3H, s) 3.33(3H, s) 4.94, 5.01(2H, ABq, J$_{AB}$=12Hz) 7.25~7.35(4H, m) | m.p. 122~124° C. Mass(FAB) m/z; 887[MH]$^+$ IR(KBr)cm$^{-1}$; 3467, 1733 | a |

TABLE 2-continued

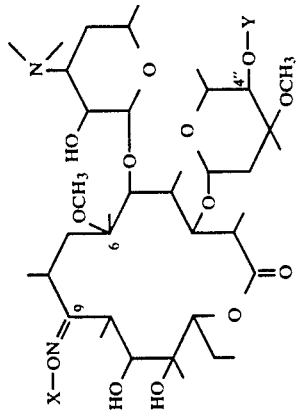

| Compound No. | X | Y | $^1$H-NMR(CDCl$_3$) δ (ppm) | Physical properties except for $^1$H NMR | Preparation method |
|---|---|---|---|---|---|
| 60 | —CH$_2$— (4-Br-C$_6$H$_4$) | H | 2.33(6H, s)<br>3.05(3H, s)<br>3.33(3H, s)<br>4.93, 4.99(2H, ABq, J$_{AB}$=12Hz)<br>7.19~7.24(2H, m)<br>7.45~7.50(2H, m) | m.p. 124~126° C.<br>(recrystallized from methanol)<br>Mass(FAB)<br>m/z; 931[MH]$^+$<br>IR(KBr) cm$^{-1}$;<br>3460, 1734 | a |
| 61 | —CH$_2$— (2,4-F$_2$-C$_6$H$_3$) | H | 2.30(6H, s)<br>3.00(3H, s)<br>3.23(3H, s)<br>5.02(2H)<br>6.77~6.90(2H, m)<br>7.31~7.39(1H, m) | m.p. 134~136° C.<br>(recrystallized from methanol)<br>Mass(FAB)<br>m/z; 889[MH]$^+$<br>IR(KBr)cm$^{-1}$;<br>3436, 1734, 1622 | a |
| 62 | —CH$_2$— (3,4-F$_2$-C$_6$H$_3$) | H | 2.31(6H, s)<br>3.05(3H, s)<br>3.33(3H, s)<br>4.92, 4.98(2H, ABq, J$_{AB}$=13Hz)<br>7.01~7.20(3H, m) | m.p. 132~134° C.<br>(recrystallized from methanol)<br>Mass(FAB)<br>m/z; 889[MH]$^+$<br>IR(KBr)cm$^{-1}$;<br>3461, 1733, 1615 | a |
| 63 | —CH$_2$— (2,5-F$_2$-C$_6$H$_3$) | H | 2.31(6H, s)<br>3.03(3H, s)<br>3.33(3H, s)<br>5.00, 5.05(2H, ABq, J$_{AB}$=13Hz)<br>6.91~7.12(3H, m) | m.p. 134~136° C.<br>(recrystallized from methanol)<br>Mass(FAB)<br>m/z; 889[MH]$^+$<br>IR(KBr)cm$^{-1}$;<br>3470, 1734 | a |

TABLE 2-continued
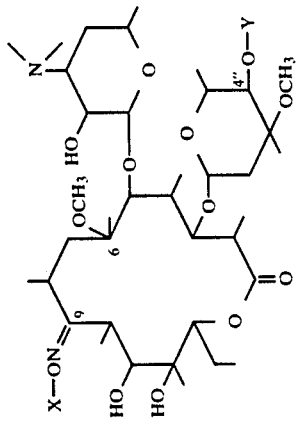
| Compound No. | X | Y | $^1$H-NMR(CDCl$_3$) δ (ppm) | Physical properties except for $^1$H NMR | Preparation method |
|---|---|---|---|---|---|
| 64 | —CH$_2$—(4-OCH$_2$CF$_3$-pyridin-2-yl) | H | 3.00(3H, s)<br>3.33(3H, s)<br>5.13(2H, s)<br>6.79(1H, dd, J=6Hz, 3Hz)<br>6.95(1H, d, J=3Hz)<br>8.44(1H, d, J=6Hz) | Mass(FAB)<br>m/z; 952[MH]$^+$<br>IR(KBr)cm$^{-1}$;<br>3446, 1734 | b |

What is claimed is:
1. A 6-0-methylerythromycin A oxide derivative represented by the formula
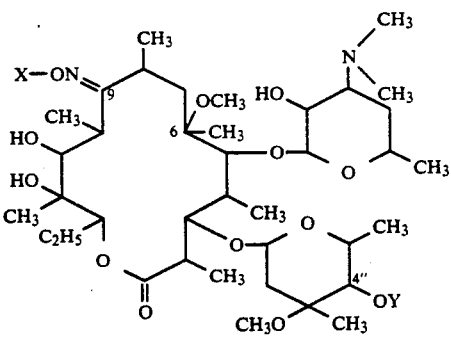
wherein X is an anthracenylmethyl group, a 2,4,6-trimethylbenzyl group or a 4-(t-butyl)benzyl group, and Y is a hydrogen atom or a pharmaceutically acceptable salt thereof.
* * * * *

UNITED STATES PATENT AND TRADEMARK OFFICE
CERTIFICATE OF CORRECTION

PATENT NO. : 5,302,705  PAGE 1 of 2
DATED : April 12, 1994
INVENTOR(S) : MISAWA et al It is certified that error appears in the above-indentified patent and that said Letters Patent is hereby corrected as shown below:

On the title page item [56]

Assistant Examiner: "Elli Pesele" should read --Elli Peselev--.

Col. 2, line 56, after "is" insert --a--.

Col. 3, line 3, "Suitable organic" should read --"Suitable organic--;

line 4, "solvent" should read --solvent"--.

Col. 7, Table 2, under the heading "$^1$H-NMR(CDCl$_3$)$\delta$(ppm)", in compound 1, line 4, delete "2.35(6H,s).

UNITED STATES PATENT AND TRADEMARK OFFICE
CERTIFICATE OF CORRECTION

PATENT NO. : 5,302,705
DATED : April 12, 1994
INVENTOR(S) : MISAWA et al

It is certified that error appears in the above-indentified patent and that said Letters Patent is hereby corrected as shown below:

Col. 10, Table 2-continued, under the heading "$^1$H-NMR(CDCl$_3$)$\delta$(ppm)", in compound 8, line 6, "6.75-6.75-6.97," should read --6.75-6.97--.

Col. 11, Table 2-continued, under the heading "$^1$H-NMR(CDCl$_3$)$\delta$(ppm)", in compound 9, line 5, "6.60" should read --6.06--.

Col. 41, line 13, "oxide" should read --oxime--.

Signed and Sealed this

Eighteenth Day of October, 1994

Attest:

BRUCE LEHMAN

*Attesting Officer*   *Commissioner of Patents and Trademarks*